(12) United States Patent
Thorne

(10) Patent No.: US 11,006,741 B1
(45) Date of Patent: May 18, 2021

(54) FLOOR CLEANER

(71) Applicant: Origyn LLC, Boston, MA (US)

(72) Inventor: Jason Thorne, Dover, MA (US)

(73) Assignee: ORIGYN LLC, Boston, MA (US)

( * ) Notice: Subject to any disclaimer, the term of this patent is extended or adjusted under 35 U.S.C. 154(b) by 0 days.

(21) Appl. No.: 17/126,355

(22) Filed: Dec. 18, 2020

Related U.S. Application Data

(60) Provisional application No. 63/043,381, filed on Jun. 24, 2020.

(51) Int. Cl.
| | |
|---|---|
| *A47L 11/22* | (2006.01) |
| *A47L 11/33* | (2006.01) |
| *A47L 13/12* | (2006.01) |
| *A46B 13/08* | (2006.01) |
| *A46B 13/00* | (2006.01) |

(52) U.S. Cl.
CPC ............ *A46B 13/08* (2013.01); *A46B 13/005* (2013.01); *A47L 11/22* (2013.01); *A47L 11/33* (2013.01); *A47L 13/12* (2013.01); *A46B 2200/302* (2013.01)

(58) Field of Classification Search
CPC . A46B 13/001; A46B 13/08; A46B 2200/302; A47L 11/22; A47L 11/33; A47L 11/4013; A47L 11/4025; A47L 11/4041; A47L 11/4069; A47L 13/12
See application file for complete search history.

(56) References Cited

U.S. PATENT DOCUMENTS

| | | |
|---|---|---|
| 588,250 A | 8/1897 | Taft |
| 4,701,969 A | 10/1987 | Berfield et al. |
| 6,041,463 A | 3/2000 | Stauch |
| 7,134,161 B2 | 11/2006 | Campos |
| 7,631,387 B2 * | 12/2009 | Sclafani et al. ......... A47L 13/12 |
| 8,020,236 B2 * | 9/2011 | Kaleta et al. ....... A47L 11/4013 |
| 8,100,446 B1 | 1/2012 | Moore et al. |
| 8,127,392 B2 | 3/2012 | Wilson |
| 8,156,596 B2 | 4/2012 | Rose |
| 8,230,540 B1 * | 7/2012 | Nelson ..................... A47L 11/33 |

(Continued)

FOREIGN PATENT DOCUMENTS

| | | |
|---|---|---|
| CN | 2353305 Y | 12/1999 |
| CN | 2652321 Y | 11/2004 |

(Continued)

OTHER PUBLICATIONS

Walmart, "Hand Push Sweeper," https://www.walmart.com/ip/Carpet-Floor-Sweeper-2-in1-Non-electric-Cordless-Hand-Push-Floor-Sweeper-Mop-Dust-Cleaner-Cleaning-Tool-for-Carpet-Wooden-Floor-Tile/209115674(accessed Dec. 7, 2020).

(Continued)

*Primary Examiner* — Randall E Chin

(74) *Attorney, Agent, or Firm* — Finch & Maloney PLLC

(57) ABSTRACT

A sweeping tool includes an elongated handle having a proximal end and a distal end, a bracket coupled to the distal end of the elongated handle, and a cleaning assembly coupled to the bracket. The cleaning assembly is designed to rotate about an axis passing through a portion of the bracket. The cleaning assembly includes a housing designed to hold a rotatable brush head and to collect debris swept up by the rotatable brush head. The cleaning assembly also includes a broom head coupled to the housing and a plurality of bristles coupled to the broom head.

20 Claims, 14 Drawing Sheets

(56) References Cited

U.S. PATENT DOCUMENTS

| | | |
|---|---|---|
| 8,533,890 B2 | 9/2013 | Pannell |
| 8,726,441 B1 | 5/2014 | Colasanti et al. |
| 8,997,294 B2 | 4/2015 | Spencer |
| 9,814,364 B1 | 11/2017 | Caruso |
| 10,016,054 B1 | 7/2018 | Parasher |
| 2005/0235440 A1* | 10/2005 | Rosenzweig et al. .. A47L 11/33 |
| 2009/0172903 A1* | 7/2009 | Vosbikian ............... A47L 13/12 |
| 2015/0265038 A1 | 9/2015 | Spinosa et al. |
| 2018/0125222 A1 | 5/2018 | Dam et al. |

FOREIGN PATENT DOCUMENTS

| | | |
|---|---|---|
| CN | 204698470 U | 10/2015 |
| CN | 205234413 U | 5/2016 |
| CN | 207101233 U | 3/2018 |
| GB | 1127570 | 10/2012 |
| WO | WO2012130123 A1 | 10/2012 |

OTHER PUBLICATIONS

Northern Tool + Equipment, "Namco Floorwash 5000 Floor Scrubber—780 RPM, 14 in. W, Model# 4588," https://www.northerntool.com/shop/tools/product_200740467_200740467 (accessed Dec. 7, 2020).
Lowes, "Shark Rechargeable Battery Carpet-and-Hand-Surface-Cordless," https://www.lowes.com/pd/Shark-Rechargeable-Battery-Carpet-and-Hard-Surface-Cordless/50147270 (accessed Dec. 7, 2020).

* cited by examiner

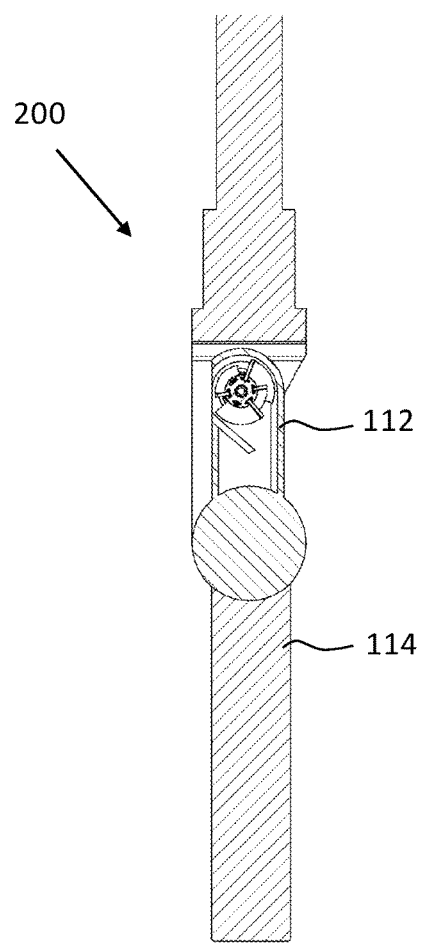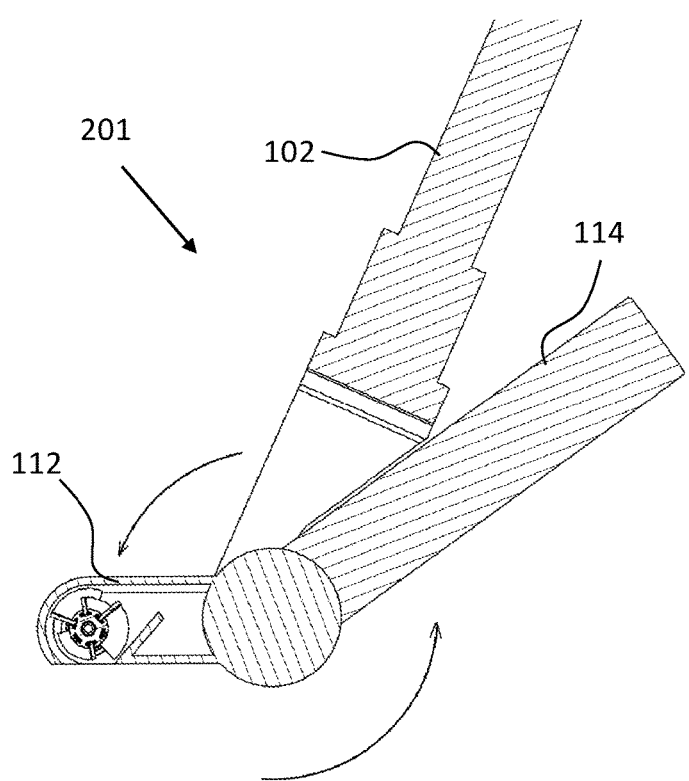
FIG. 2A                    FIG. 2B

FLOOR CLEANER

CROSS REFERENCE TO RELATED APPLICATION

This application claims the benefit of U.S. Provisional Application No. 63/043,381, filed Jun. 24, 2020, the disclosure of which is incorporated by reference herein in its entirety.

BACKGROUND

Cleaning tools such as brooms and sweeper devices have been used for decades to aid in cleaning dirt and other debris from floors. Brooms typically require a dustpan or other similar receptacle to place the dirt in after being swept by the broom. Sweepers may have a built-in area to collect dirt, but the units are often heavy, bulky, and expensive. Accordingly, there exist some drawbacks and other unsolved issues that limit the convenience of brooms and sweeping tools.

BRIEF DESCRIPTION OF THE DRAWINGS

Features and advantages of embodiments of the claimed subject matter will become apparent as the following Detailed Description proceeds, and upon reference to the Drawings, in which:

FIGS. 2A and 2B illustrate different positions of a broom and brush assembly on the sweeping tool, in accordance with some embodiments of the present disclosure.

Figure 1A:
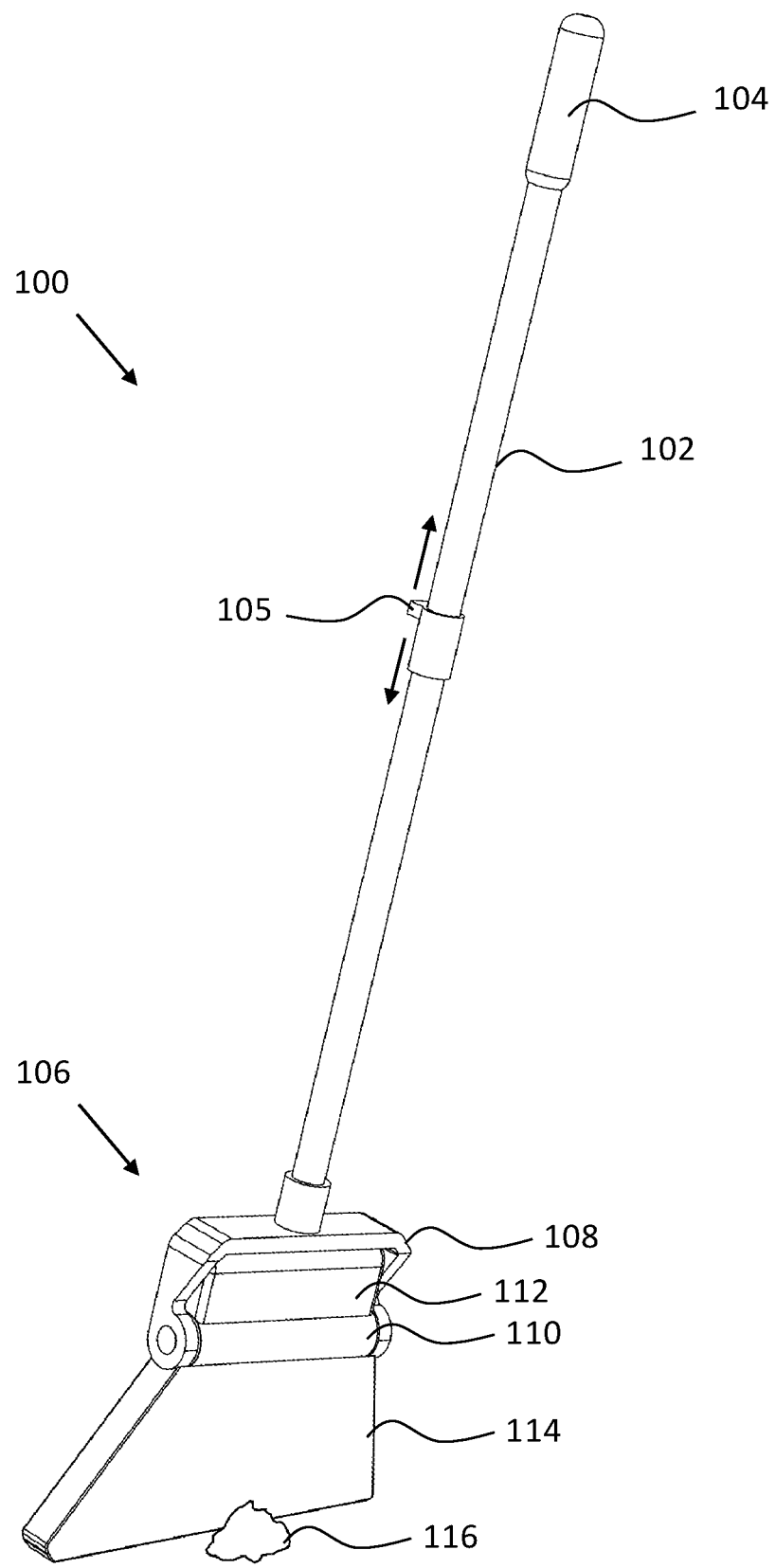
FIGS. 1A and 1B illustrate different perspective, three-dimensional views of a sweeping tool, in accordance with some embodiments of the present disclosure.

Although the following Detailed Description will proceed with reference being made to illustrative embodiments, many alternatives, modifications, and variations thereof will be apparent in light of this disclosure.

DETAILED DESCRIPTION

As noted above, there are some non-trivial issues with cleaning equipment such as brooms and sweepers. Many of the issues pertain to matters of convenience for the user. For example, brooms may require the use of a separate dustpan to hold the swept debris. Hand held dustpans require the user to get down on their hands and knees while dustpans on longer poles are cumbersome. Sweeper systems may provide their own debris receptacle, but such systems are often unwieldy and expensive. Accordingly, a sweeper design is provided herein that combines the advantages of a broom with that of a sweeper brush to provide a light-weight and affordable cleaning solution. Some of the advantages of a broom include the ability to reach under and around objects and the fact that a broom is always ready to use (e.g., no need for power). The sweeper design described in various embodiments herein keep all the advantages of the broom while eliminating its primary disadvantage—the need for a separate dustpan. In an example embodiment, a sweeping tool includes an elongated handle having a proximal end and a distal end, a bracket coupled to the distal end of the elongated handle, a broom head coupled to the bracket, and a brush assembly coupled to the bracket. The broom head is configured to rotate about an axis passing through the bracket. The brush assembly includes a rotatable brush head and a catch tray designed to collect debris swept up by the rotatable brush head.

In another example embodiment, a sweeping tool includes an elongated handle having a proximal end and a distal end, a bracket coupled to the distal end of the elongated handle, and a cleaning assembly coupled to the bracket. The cleaning assembly is designed to rotate about an axis passing through the bracket. The cleaning assembly includes a housing with a first portion designed to hold a rotatable brush head and a second portion designed to collect debris swept up by the rotatable brush head. The cleaning assembly also includes a broom head extending away from the housing and a plurality of bristles coupled to the broom head.

According to some embodiments, the sweeping tool disclosed herein can quickly and easily change between a broom and a brush sweeper at any time. A mechanical lever or similar structure on the handle of the sweeping tool allows a user to easily switch between broom mode or sweeper mode to pick debris up off the floor. For example, the sweeping tool may be used in broom mode to collect debris into a pile on the floor. Then, the user can switch the sweeping tool into the sweeper mode which rotates the broom out of the way and allows a brush sweeper to engage the floor and sweep the debris into a catch tray. All of this can be performed quickly and without needing to change between any tools. Furthermore, the mechanical design allows for a cordless system that does not require any electrical power. These and other such embodiments will be described in more detail herein.

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. When used to describe a range of dimensions, the phrase "between X and Y" represents a range that includes X and Y.

Spatially relative terms, such as "beneath," "below," "lower," "above," "upper," and the like, may be used herein for ease of description to describe one element or feature's relationship to another element (s) or feature (s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 1A illustrates a perspective three-dimensional view of a sweeping tool 100, according to an embodiment. Sweeping tool 100 includes an elongated handle 102 to allow for user to comfortably grasp elongated handle 102 at two positions to perform sweeping motions or pushing motions with sweeping tool 100. Elongated handle 102 may be formed of any sufficiently stiff material, such as metal, wood, or hard plastic. In some embodiments, elongated handle 102 is made from aluminum.

One end of elongated handle 102 includes a grip 104, according to an embodiment. Grip 104 may be ergonomically designed for an adult hand and may be made from a softer material compared to elongated handle 102. In some embodiments, a second grip (not illustrated) is located along the length of elongated handle 102 such that both hands can be comfortably placed with one hand on grip 104 and the second hand on the second grip. In some embodiments, elongated handle 102 includes telescoping portions to adapt its length. In some embodiments, elongated handle 102 has a length between about 50" and about 60".

According to some embodiments, a bracket 108 is coupled to a distal end 106 of elongated handle 102. Bracket 108 may have a 'U' shape to allow for a brush assembly 112 to rotate into and out of the opening formed within the 'U' shape. A top, flattened end of the 'U' shape may be coupled directly to distal end 106 of elongated handle 102. In some embodiments, bracket 108 is formed from a metal, such as stainless steel.

According to some embodiments, a broom head 110 is coupled to a lower portion of bracket 108, which allows broom head 110 to rotate about an axis passing through the lower portion of bracket 108. Broom head 110 may include a plurality of bristles 114 extending out from one side of broom head 110. Bristles 114 may be fanned out to form a typical broom shape.

According to some embodiments, a lever 105 is movable along a length of elongated handle 102 (e.g., slidable along the length of elongated handle 102) to switch sweeping tool 100 between a first state and a second state. FIG. 1A illustrates an example first state of sweeping tool 100 where bristles 114 are extended down substantially parallel (e.g., within 5 degrees of being parallel) to elongated handle 102 and brush assembly 112 is retained in bracket 108. Broom head 110 may be locked into the illustrated first state such that sweeping can occur in either direction without rotating either broom head 110 or brush assembly 112. Accordingly, in its first state, sweeping tool 100 can be used like a traditional broom to sweep up debris 116 on any floor surface. Furthermore, in its first state, sweeping tool 100 can lie substantially flat against a wall surface for easy storage. According to an embodiment, movement of lever 105 transitions sweeping tool 100 between the first state and a second state where broom head 110 rotates to bring brush assembly down towards the floor surface while simultaneously rotating bristles 114 up and out of the way. Lever 105 can take on any mechanical form and may also represent spring-loaded push buttons to change between the first state and the second state, and the broom head can be locked in either position. In another example, lever 105 includes a coaxial tubular shape around elongated handle 102 that slides along the length of elongated handle 102 to switch broom head 110 between a first state and a second state.

Figure 1B:
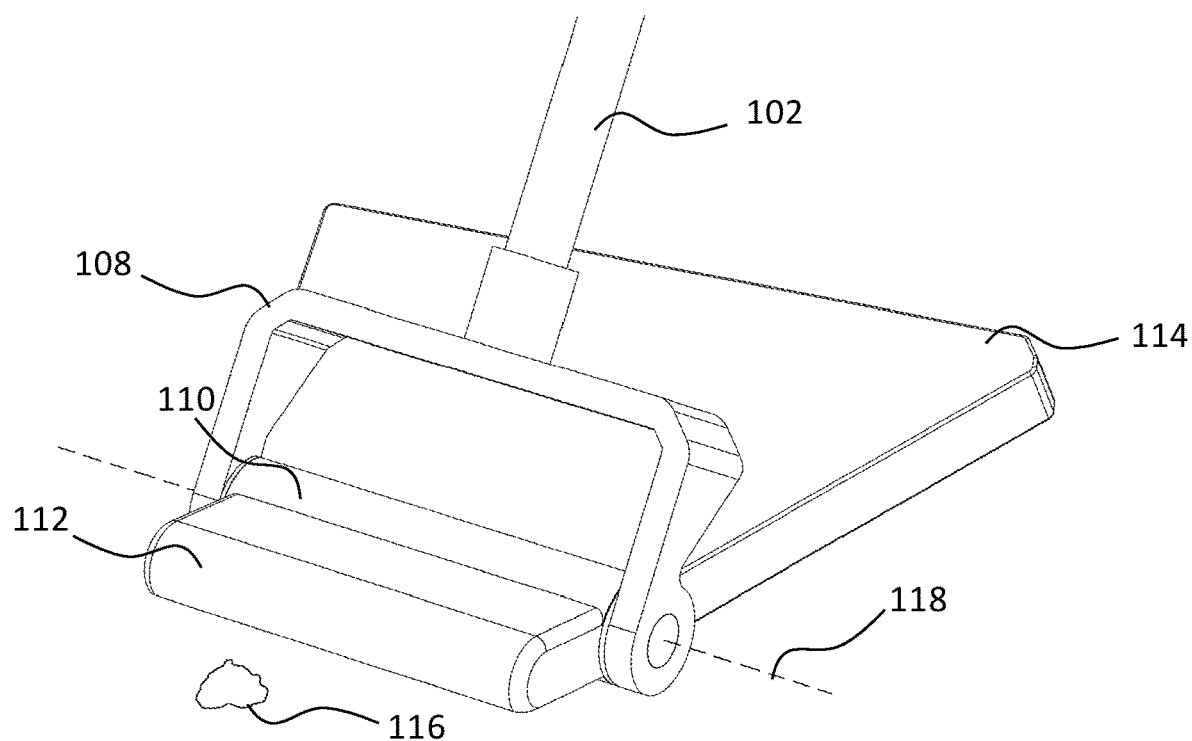

FIG. 1B illustrates a lower portion of sweeping tool 100 in its second state, according to an embodiment. Broom head 110 may be locked into the illustrated second state such that pushing sweeping tool 100 across a floor surface occurs without rotating either broom head 110 or brush assembly 112. Accordingly, broom head 110 may be locked into the first state, locked into the second state, or transitioning between the first state and the second state. During the transition period, broom head 110 rotates about an axis 118 to bring brush assembly 112 from a first state between bracket 108 to a second state down towards the floor. According to an embodiment, since bristles 114 are attached to one end of broom head 110, the rotation of broom head 110 also causes bristles 114 to rotate about axis 118 such that they do not contact the floor when pushing brush assembly 112 across the floor to brush up debris 116. In some embodiments, when sweeping tool 100 is locked into the second state, bristles 114 are rotated up to a position that is at an acute angle with respect to elongated handle 102. In some embodiments, bracket 108 is free to rotate about axis 118 while brush assembly 112 and broom head 110 are locked in the second state. The free rotation of bracket 108 allows for elongated handle 102 to rotate along with bracket 108 and can be used to rotate elongated handle towards the floor to push brush assembly 112 under furniture or other obstacles that would otherwise hinder progress. In one example, bracket 108 may rotate such that elongated handle 102 is substantially parallel with bristles 114 while broom head 110 is locked in the second state. In another example, bracket 108 may rotate into a position that is substantially perpendicular to brush assembly 112, thus allowing sweeping tool 100 to stand on its own.

Figure 1C:
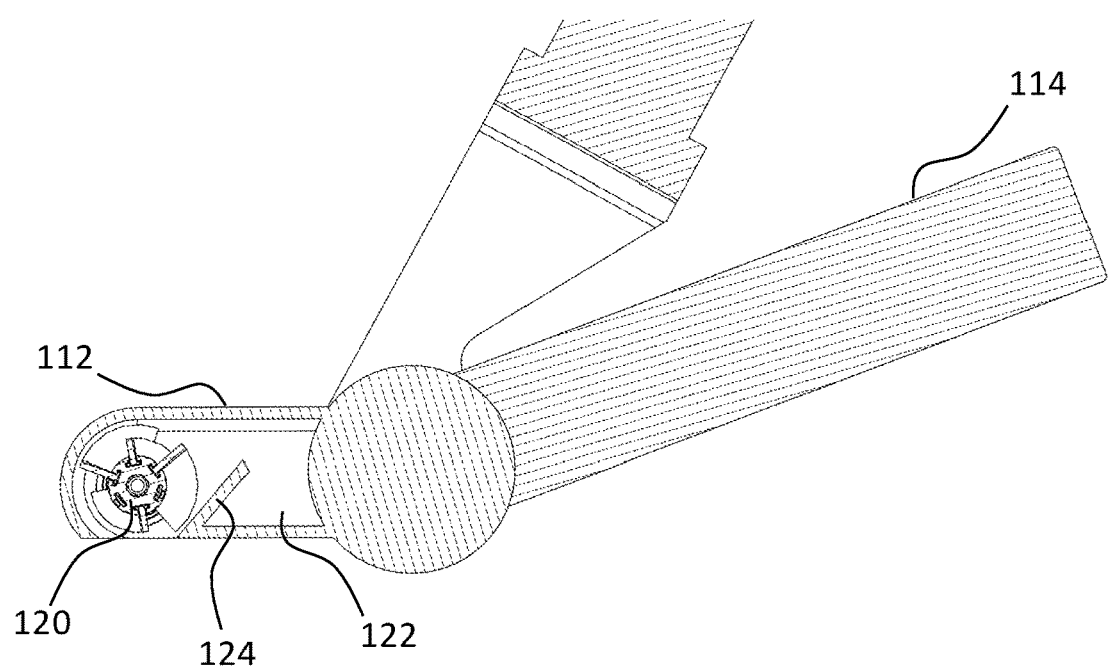
FIG. 1C illustrates a three-dimensional cut-away view of the sweeping tool, in accordance with some embodiments of the present disclosure.

FIG. 1C illustrates a cutaway view of an interior portion of brush assembly 112, according to an embodiment. Brush assembly 112 includes a rotatable brush head 120 and a catch tray 122. Rotatable brush head 120 may include any number of brushes or bristles radially extending out from a tubular structure that rotates to move the brushes or bristles in a continuous circular direction. The rotating brushes or bristles of rotatable brush head 120 sweep up any debris in their path and deposit the debris within catch tray 122 on the other side of an inclined dividing wall 124. In some embodiments, rotatable brush head 120 can rotate in a counter-clockwise direction to direct the debris up dividing wall 124 and into catch tray 122. In some embodiments, movement of brush assembly 112 across a floor surface causes rotation of rotatable brush head 120. In some embodiments, rotatable brush head 120 is coupled to wheels that move along the floor surface, such that rotation of the wheels cause a corresponding rotation of rotatable brush head 120.

FIG. 2A illustrates another view of sweeping tool 100 when locked into a first state 200. In this position, brush assembly 112 may be parallel with bristles 114 such that it is pointing upwards towards elongated handle 102 and is out of the way when using bristles 114 to sweep up debris. FIG. 2B illustrates another view of sweeping tool 100 when locked into a second state 201. In this position, brush assembly 112 is rotated down towards the floor until brush assembly 112 is substantially parallel with the floor. Meanwhile, bristles 114 may be rotated upwards away from the floor and lock into a position where bristles 114 make an acute angle with respect to elongated handle 102. According to some embodiments, brush assembly 112 and bristles 114 are coupled together via a common assembly that rotates, thus causing the same corresponding rotation to both brush assembly 112 and bristles 114. According to some embodiments, bristles 114 remain at a 180-degree orientation with respect to brush assembly 112 in second state 201.

Figure 3A:
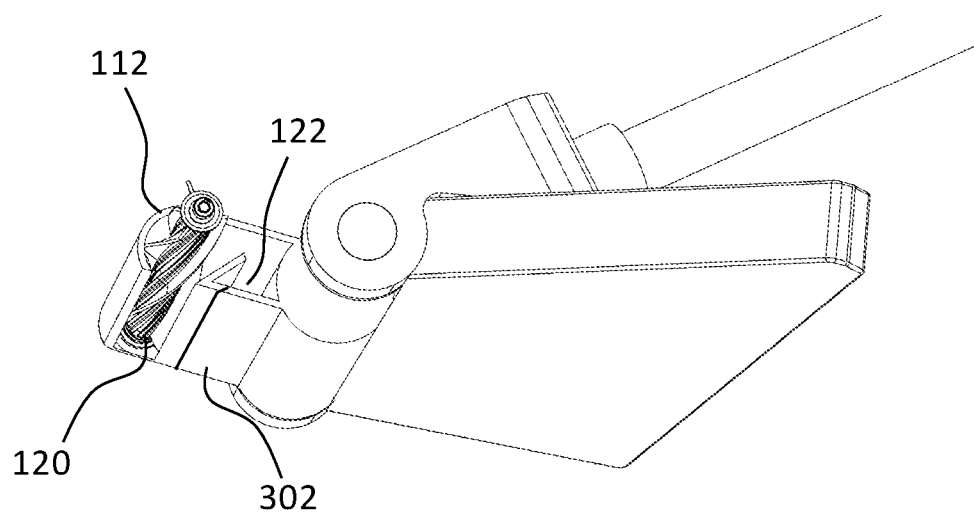
FIGS. 3A and 3B illustrate views of a release door as part of a debris catch tray, in accordance with some embodiments of the present disclosure.
Figure 3B:
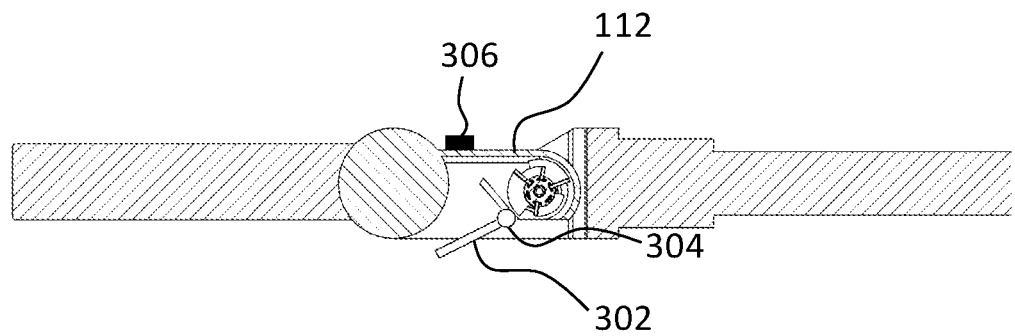

FIG. 3A illustrates a view of an underside of brush assembly 112, according to an embodiment. Brush assembly 112 may include a door 302 that can be opened to empty any debris within catch tray 122. Door 302 may be flush with a housing of brush assembly 112 in its closed state and may rotate about a hinged axis to open and drop whatever is stored within catch tray 122. FIG. 3B illustrates another view of brush assembly 112 showing how door 302 can rotate about hinge(s) 304 to open and close. In some embodiments, a button 306 may be provided on brush assembly 112 to cause door 302 to open when button 306 is pressed. In some embodiments, pushing button 306 again causes door 302 to close. Button 306 may be located on any part of brush assembly 112, such as on a side or top surface. In some other embodiments, door 302 is manually closed by moving it back into its closed position where it locks into place. Pushing button 306 unlocks door 302 from its locked position and causes it to freely swing downward about an axis passing through hinge(s) 304. Although button 306 is depicted on brush assembly 112, this location is not required, and button 306 may be located anywhere on sweeping tool 100, such as on elongated handle 102. Door 302 or lateral parts of the housing, for example, can be made from transparent material so that the user can observe how full catch tray 122 is.

Figure 4A:
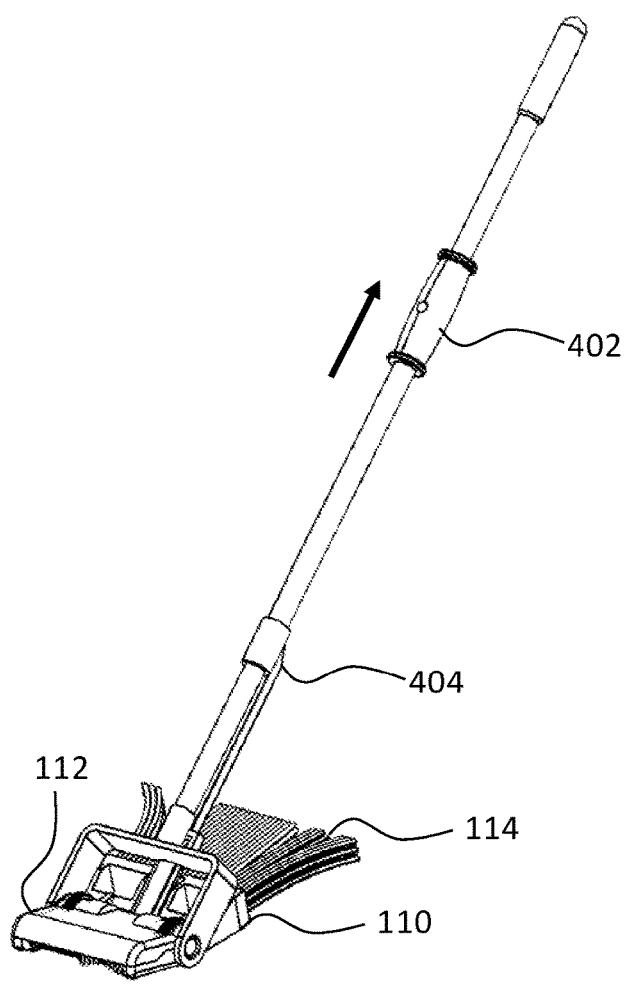
FIGS. 4A and 4B illustrate different perspective, three-dimensional views of the sweeping tool, in accordance with some embodiments of the present disclosure.
Figure 4B:
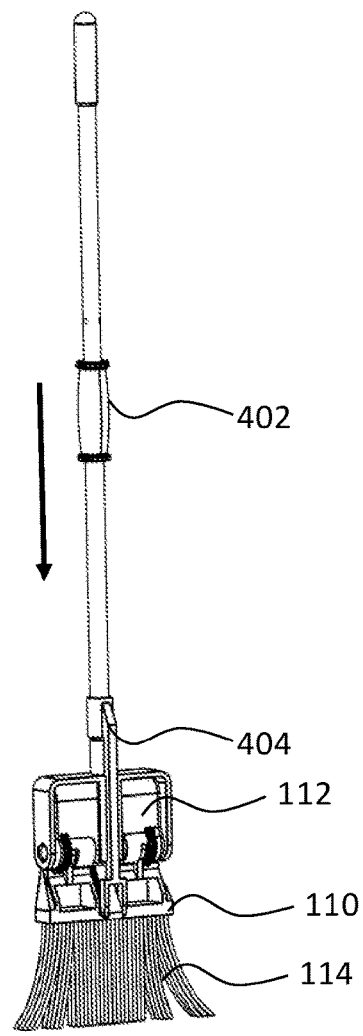

FIGS. 4A and 4B illustrate different views of another example of a sweeping tool that includes a slidable grip 402 designed to slide along at least a portion of the length of elongated handle 102 to switch between a second state (illustrated in FIG. 4A) and a first state (illustrated in FIG. 4B), according to some embodiments. Slidable grip 402 may be coupled to another slidable lever 404. Movement of slidable grip 402 causes a corresponding movement to slidable lever 404, which is mechanically linked to a portion of broom head 110 and/or brush assembly 112 that is offset from the axis of rotation as seen, for example, in FIG. 1B. When slidable lever 404 is pulled upwards as shown in FIG. 4A, it pulls on broom head 110 and causes it to rotate, moving bristles 114 up towards elongated handle 102 and moving brush assembly 112 down towards the floor. When slidable lever 404 is pushed downwards as shown in FIG. 4B, it pushes broom head 110 and bristles 114 back into a position where bristles are substantially parallel to elongated handle 102. Additionally, brush assembly 112 is rotated back up between bracket 108 and away from the floor surface when slidable lever 404 is pushed downwards.

Figure 5A:
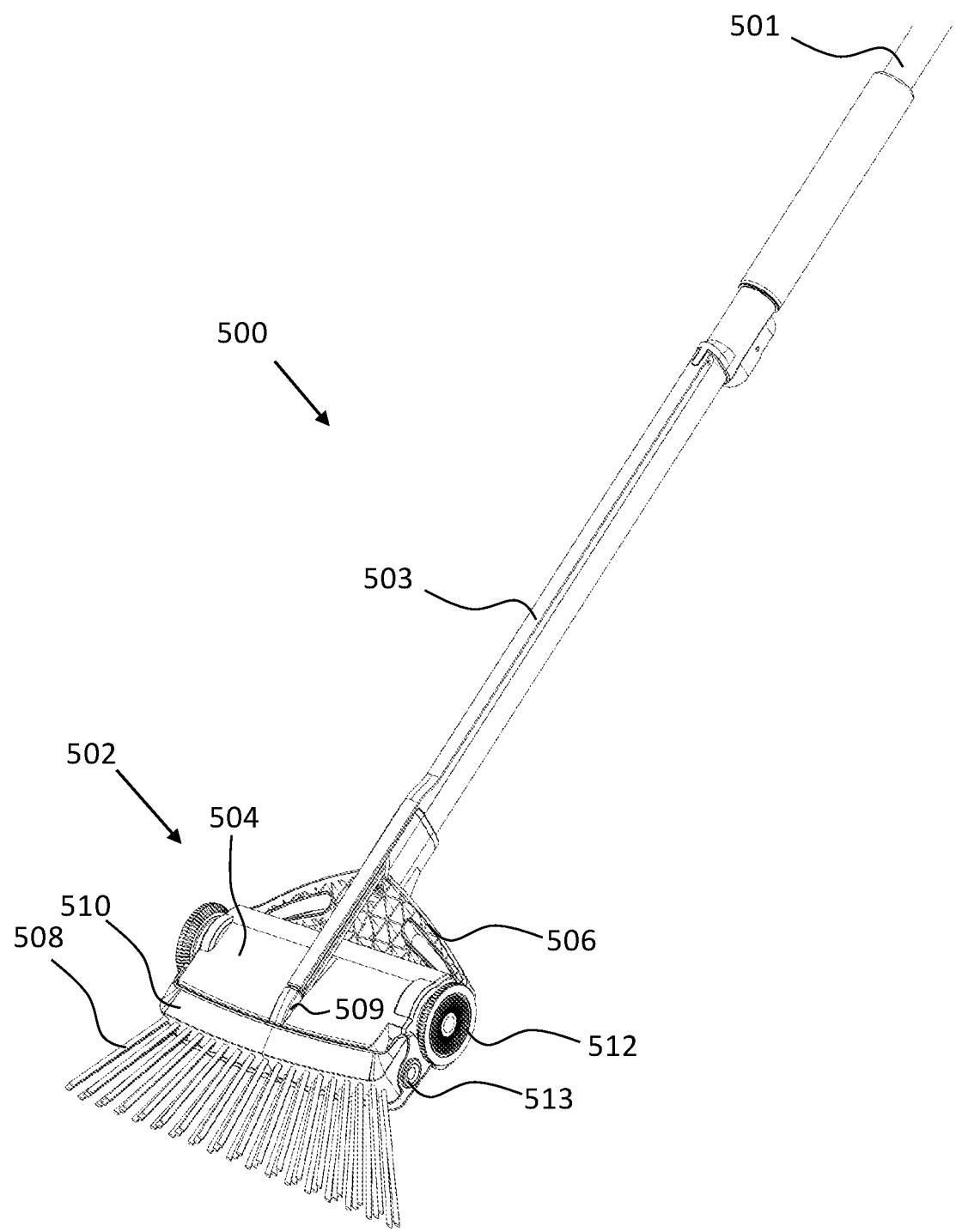
FIGS. 5A-5C illustrate three-dimensional views of another sweeping tool design, in accordance with some embodiments of the present disclosure.
Figure 5B:
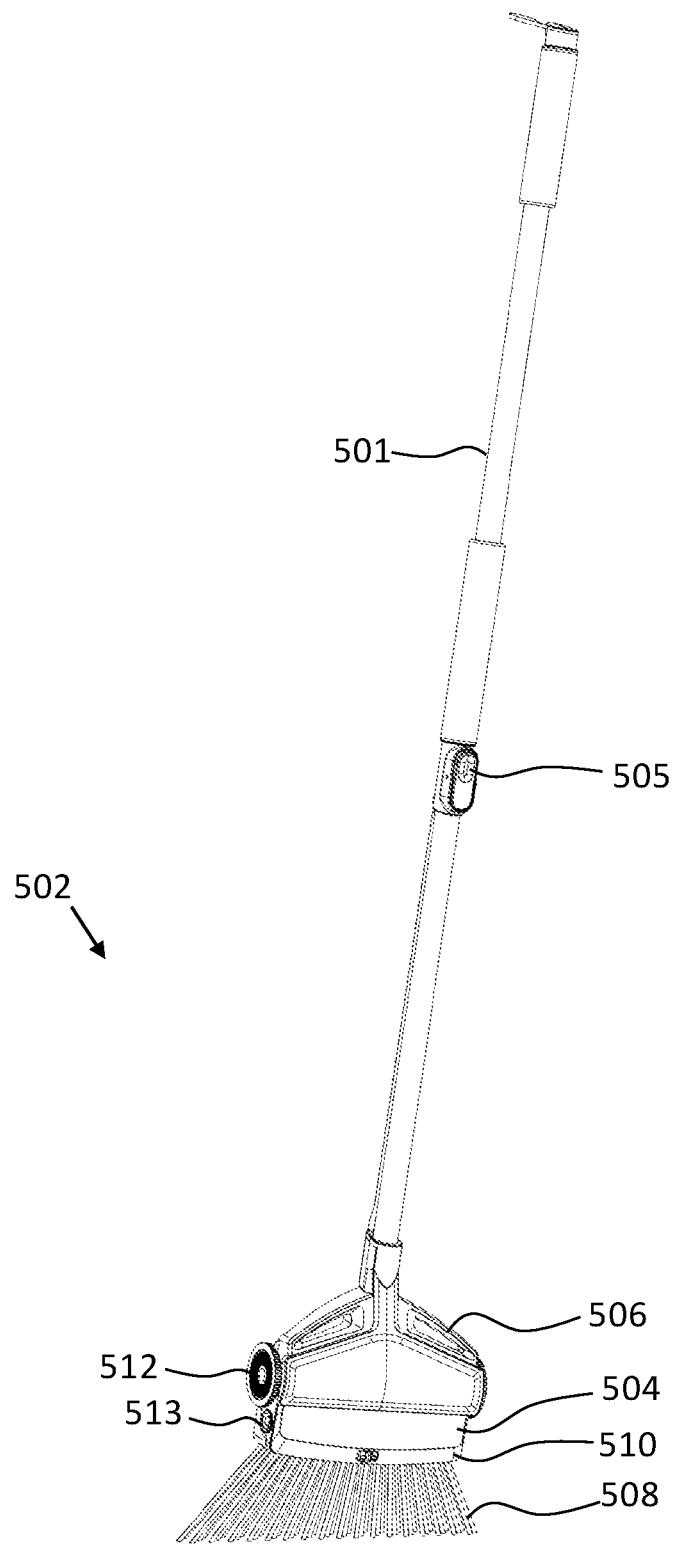

FIGS. 5A and 5B illustrate underneath and topside views, respectively, of another example of a sweeping tool 500 locked into its first state such that it can be used as a broom to sweep debris, according to some embodiments. Sweeping tool 500 may include any of the features as described above for sweeping tool 100, except that sweeping tool 500 includes a cleaning assembly 502 having a housing 504 that rotates about an axis passing through a bracket 506, according to an embodiment. Accordingly, a distal end of an elongated handle 501 includes bracket 506, such as a 'U' shaped bracket, and cleaning assembly 502 coupled to bracket 506. Cleaning assembly 502 may be locked into a first state as illustrated in both FIGS. 5A and 5B where bristles 508 extending from a broom head 510 are used to sweep debris like a standard broom. Both bracket 506 and housing 504 may be formed from an injection molded plastic, such as acrylonitrile butadiene styrene (ABS).

Figure 5C:
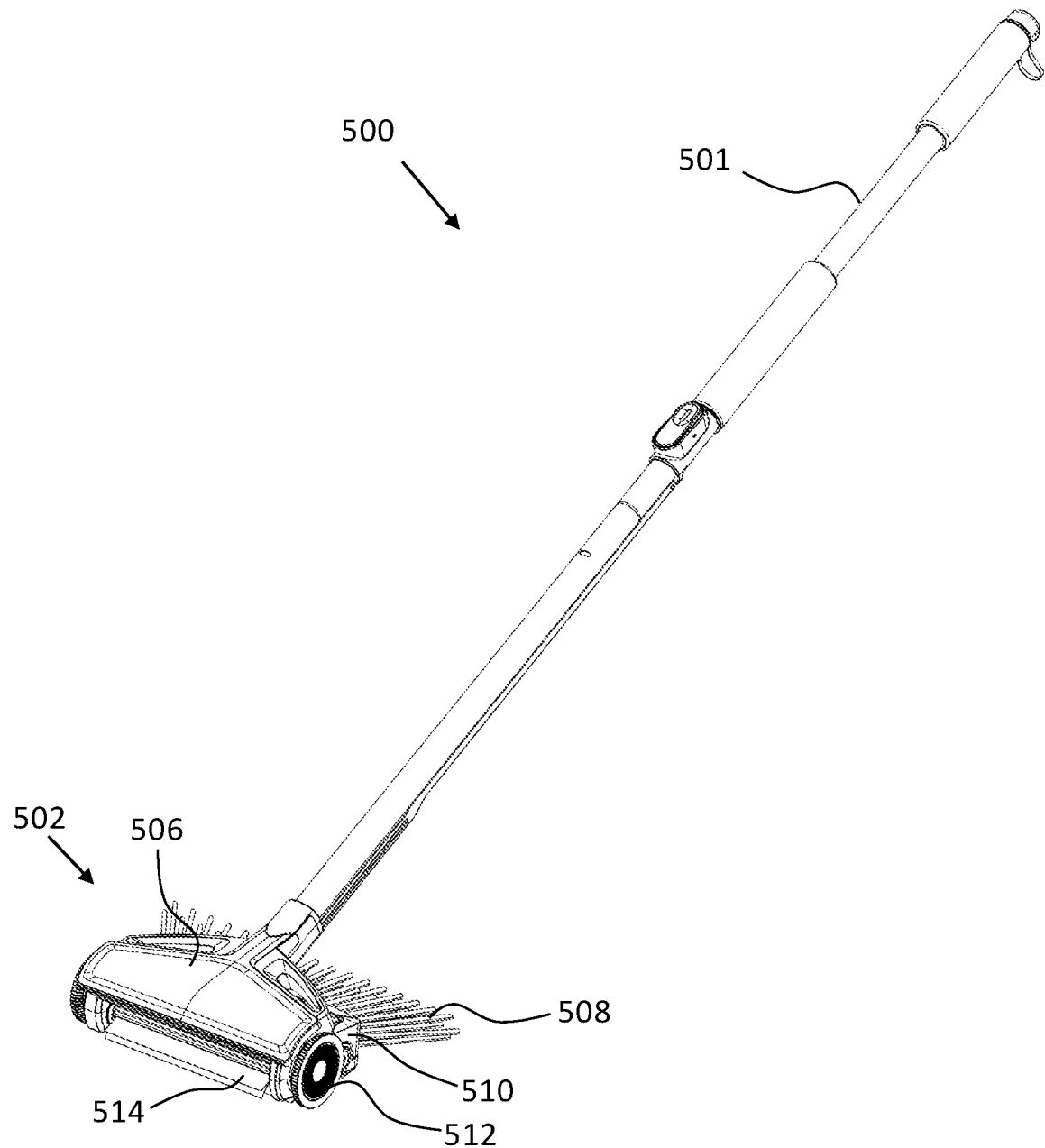

As described above, movement of a lever assembly 503 axially along elongated handle 501 unlocks sweeping tool 500 from its first state and allows for cleaning assembly 502 to rotate about an axis passing through bracket 506. Lever assembly 503 may include an elongated rod connected at one end to a moveable structure (activated via button 505) on elongated handle 501 and engaged with a catch (not shown) on the underside of housing 504 at the opposite end. Briefly, and in accordance with some embodiments, lever assembly 503 is coupled to the catch within a curved housing 509 on the underside of housing 504 when sweeping tool 500 is locked into its first state. A button 505 is pressed and/or slid upwards along a portion of elongated handle 501 to release the catch and enable a corresponding mechanical sliding movement of lever assembly 503. This sliding motion of lever assembly 503 disengages lever assembly 503 from within curved housing 509 and slides it up and out of the way of cleaning assembly 502 so that cleaning assembly 502 can rotate freely into its second state, as shown in FIG. 5C. A view of lever assembly 503 retracted away from cleaning assembly 502 while cleaning assembly 502 is rotated into its second state is more clearly illustrated in FIG. 5D. To move cleaning assembly 502 back to its first state, button 505 is pressed and/or slid downwards along the length of elongated handle 501 to cause lever assembly 503 to slide back across the underside of housing 504 and re-engage with the catch within curved housing 509, according to an embodiment.

In some embodiments, sweeping tool 500 includes wheels 512 coupled to either side of bracket 506. In some embodiments, cleaning assembly 502 rotates about an axis that also passes through a center of wheels 512. Accordingly, wheels 512 act as a kind of pivot point around about which cleaning assembly 502 pivotally rotates to move from its first state into its second state. According to some embodiments, a button 513 is provided on either or both sides of housing 504. Button 513 may be pressed to open a door to a catch tray and release the contents therein, as shown in more detail with reference to FIG. 5D.

FIG. 5C illustrates an example of sweeping tool 500 where cleaning assembly 502 has been moved into a second state such that sweeping tool 500 can be pushed along the floor to brush up debris, according to an embodiment. Note that, in some embodiments, cleaning assembly 502 does not need to be locked in place when moved to the second state as the floor maintains the position of cleaning assembly 502. In some embodiments, when removed from the floor surface, cleaning assembly freely rotates back to its first position, such that lever assembly 503 can be slid back across the underside of housing 504 to re-engage with the catch. Housing 504 (mostly obscured from view in FIG. 5C by bracket 506) includes a rotatable brush head 514. In its second state, cleaning assembly 502 rests upon wheels 512, such that pushing sweeping tool 500 across the floor causes a corresponding rotation of wheels 512. Wheels 512 may include tires or a coating of a material to provide a high coefficient of friction with the floor. For instance, the wheels can include a polymeric material such as silicone rubber or polyvinylchloride (PVC). In some embodiments, wheels 512 are coupled to rotatable brush head 514 such that rotation of wheels 512 causes a corresponding rotation of rotatable brush head 514 using one or more gears or belts as shown in more detail with reference to FIG. 7. The turn ratio between the wheels and the brush can be greater than or less than 0.5:1, greater than or less than 1:1, greater than or less than 2:1 or greater than or less than 3:1. In some embodiments, the gears are disengaged on the backstroke to avoid redepositing debris onto the floor from cleaning assembly 502. In other embodiments, a simple transmission can allow either forward or reverse motion of the wheels to drive brush head 514 in the same direction, either clockwise or counterclockwise. When in its second state, cleaning assembly 502 rotates such that broom head 510 moves to a position that faces back towards elongated handle 501. As noted above, in some embodiments, elongated handle 501 along with bracket 506 are free to rotate about an axis passing through wheels 512 when cleaning assembly 502 is in the second state.

Figure 5D:
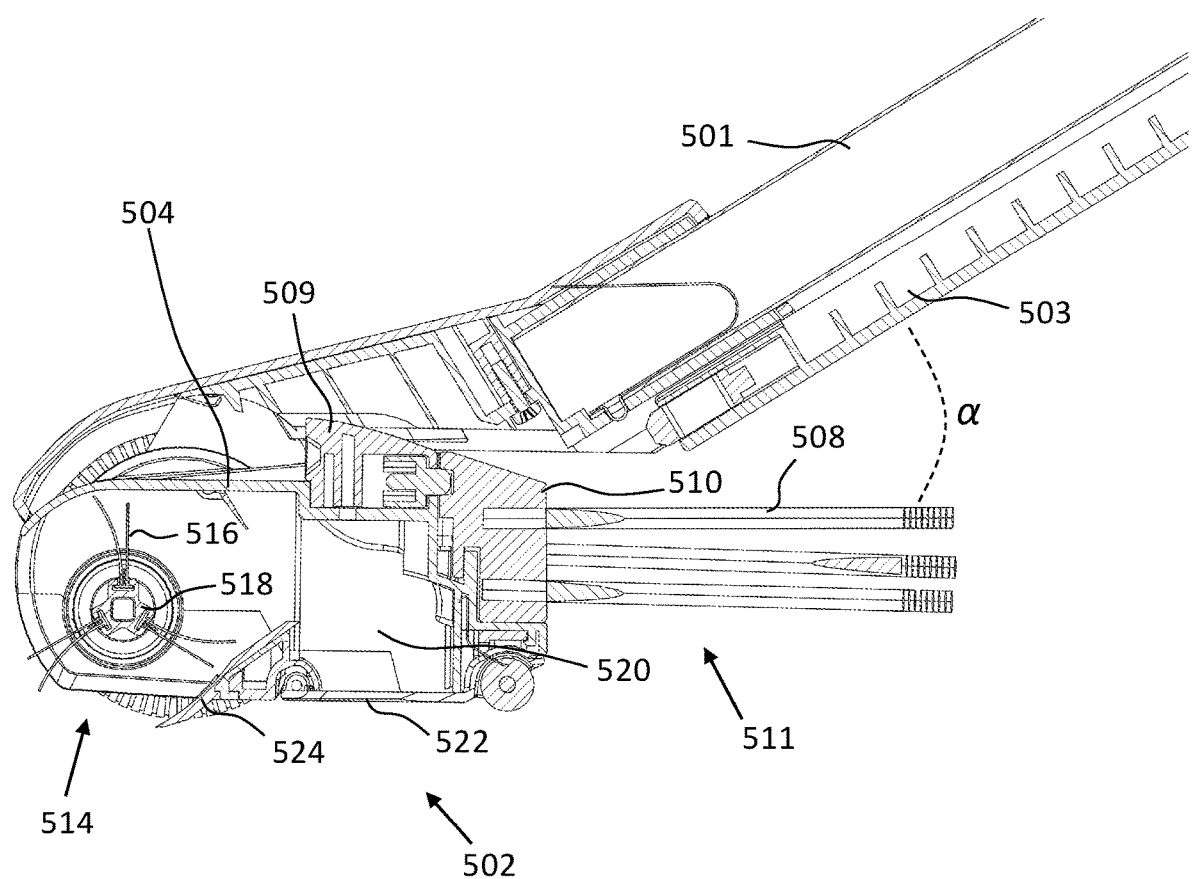
FIG. 5D illustrates a three-dimensional cut-away view of the sweeping tool of FIGS. 5A-5C, in accordance with some embodiments of the present disclosure.

FIG. 5D illustrates a cutaway view of cleaning assembly 502 in its second state, according to an embodiment. Depending on the orientation of elongated handle 501, bristles 508 may make an acute angle with respect to elongated handle 501 when in the second state. For example, bristles 508 may be rotated to an angle α of at least 30 degrees, at least 45 degrees, at least 60 degrees, at least 90 degrees, or at least 120 degrees with respect to elongated handle 501. Lever assembly 503 is seen slid up and away from cleaning assembly 502 along elongated handle 501. Rotatable brush head 514 is seen within housing 504 of cleaning assembly 502. Rotatable brush head 514 includes a plurality of brushes or bristles 516 coupled to a rotating bar 518. Rotation of rotatable brush head 514 moves debris from the floor up and into catch tray 520 within housing 504 of cleaning assembly 502.

According to some embodiments, housing 504 includes a release door 522 that can be opened to empty any debris captured within catch tray 520. Release door 522 may be hinged on one side to swing open about an axis passing through the hinge. A small lever or button may be present either along elongated handle 501 or on cleaning assembly 502 to allow release door 522 to swing open. In some embodiments, release door 522 may be manually shut and kept in a closed position via any type of latch structure.

In some embodiments, cleaning assembly 502 further includes a wedge plate 524 that is designed to scrape along the ground as cleaning assembly 502 is moved across the floor. Wedge plate 524 may be formed from any pliable material and is provided at an angle so as to assist brush head 514 in transporting debris from the floor up and into catch tray 520.

Broom head 510 and coupled bristles 508 are components of a broom module 511 that can be detached from housing 504. According to some embodiments, broom module 511 can be decoupled from housing 504 and replaced by a different broom module. In one example, a broom module having soft bristles may be attached to housing 504 for use on certain surfaces like hardwood floors. In another example, a broom module having slightly thicker bristles may be attached to housing 504 to sweep debris out from crevices or other rough areas. In yet another example, a broom module having a foam attachment may be attached to housing 504 to collect lighter debris like pet hair and dander. In some other embodiments, housing 504 and broom head 510 are formed from a single molded material.

Figure 6A:
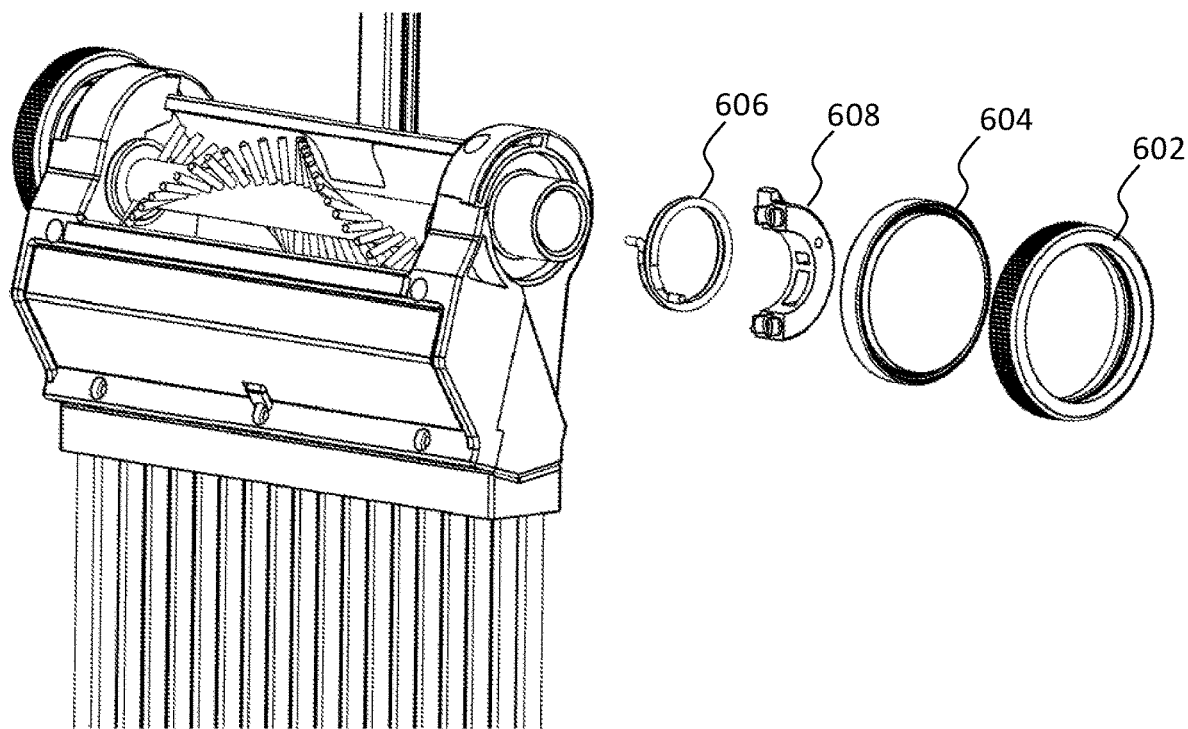
FIGS. 6A and 6B illustrate different exploded views of a wheel assembly of a sweeping tool, in accordance with some embodiments of the present disclosure.
Figure 6B:
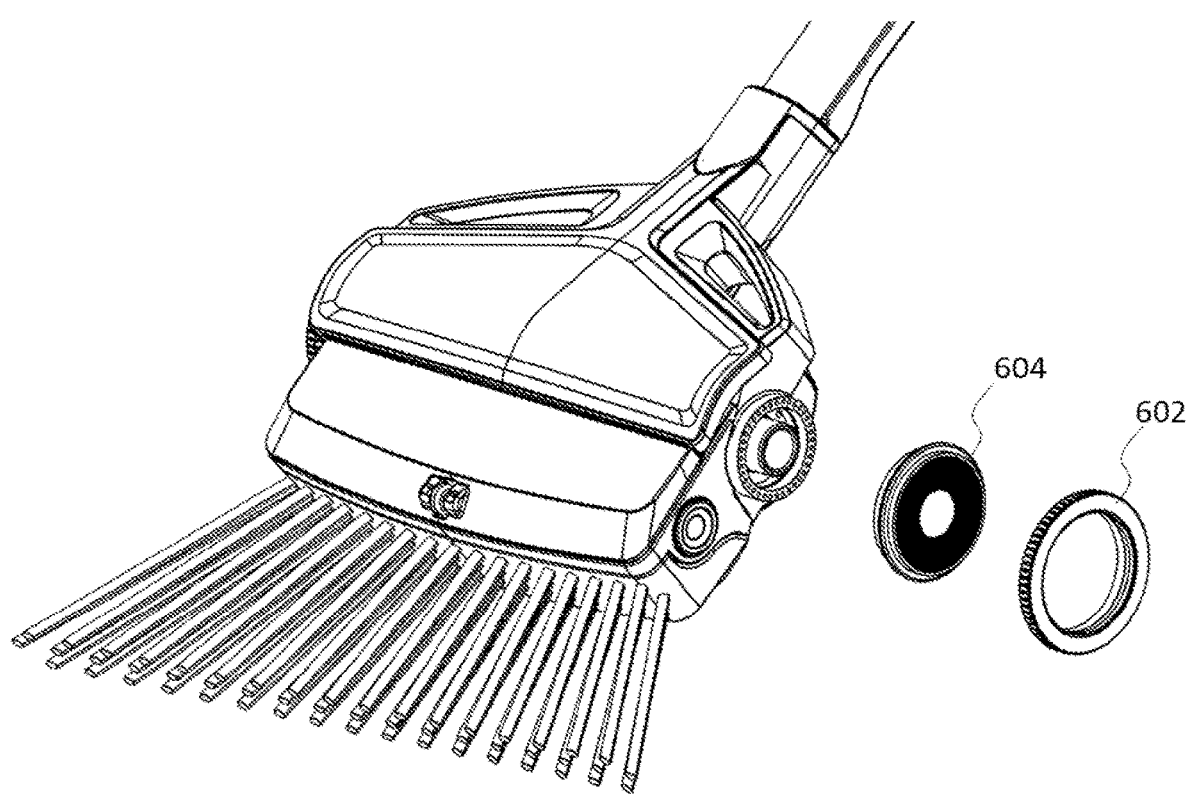

According to some embodiments, one of wheels 512 includes a torsion spring while the other of wheels 512 includes a set of gears to rotate rotatable brush head 514 along with the rotation of the wheel. FIGS. 6A and 6B illustrate exploded views of one of the wheels 512, according to an embodiment. FIG. 6A illustrates an optional wheel design that includes a torsion spring 606 while FIG. 6B illustrates a wheel without a torsion spring. As seen in FIG. 6A, the wheel includes an outer tire 602 that may be any polymer or rubberized material. Outer tire 602 wraps around a cylinder 604 that forms the structure of the wheel. The wheel also includes torsion spring 606 that is housed partially within a bracket cover 608. In some embodiments, torsion spring 606 is used to maintain the angular position of (e.g., by holding the weight of) broom head 510 and its bristles 508 when cleaning assembly 502 is in the second state. FIG. 6B illustrates another embodiment of a wheel that just includes outer tire 602 wrapped around cylinder 604 without any torsion spring assembly. In either embodiment, the opposite wheel includes one or more gears for turning rotatable brush head 514.

Figure 7:
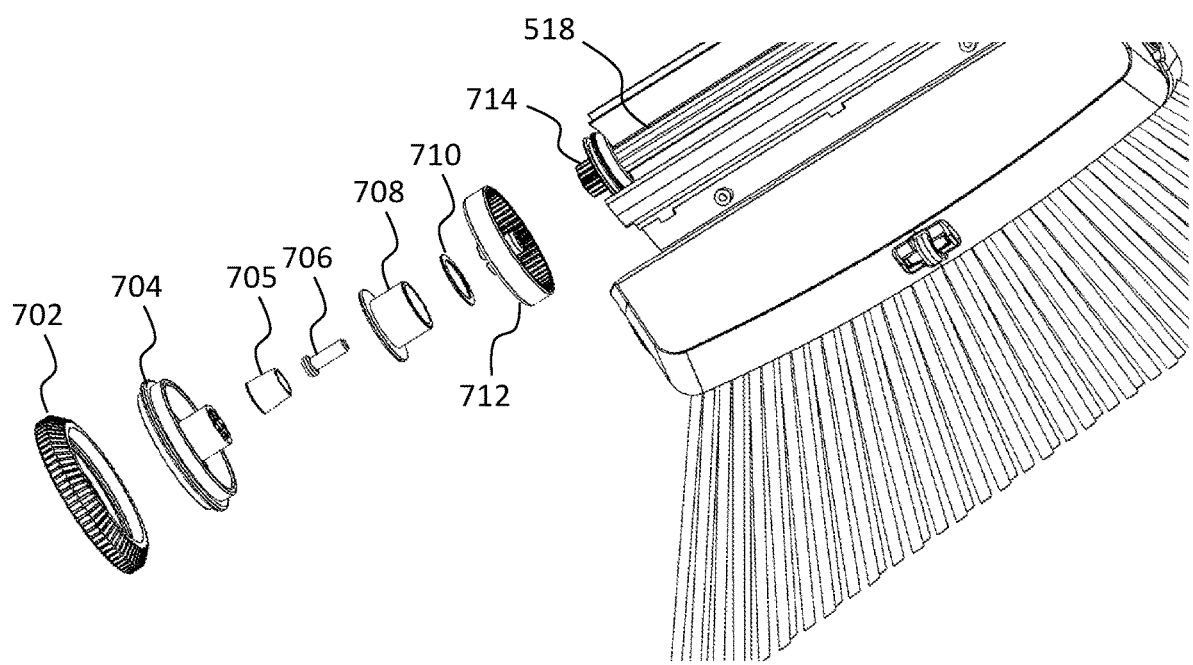
FIG. 7 illustrates an exploded view of another wheel assembly of the sweeping tool opposite to the wheel assembly from FIGS. 6A and 6B, in accordance with some embodiments of the present disclosure.

FIG. 7 illustrates an exploded view of the opposite wheel which includes the one or more gears, according to an embodiment. The opposite wheel also includes an outer tire 702 and a cylinder 704 similar to those described above for the other wheel. A drive wheel cap 705 may be disposed within a central portion of cylinder 704. In some embodiments, the wheel includes a fastener 706, such as a screw, that holds the components together. Cylinder 704 fits within a wheel sleeve 708 that rests against a large gear 712. In some embodiments, wheel sleeve 708 rests directly on a washer 710 between wheel sleeve 708 and large gear 712. According to an embodiment, the inner circumference of large gear 712 includes gear teeth that engage with the teeth of a smaller gear 714. Smaller gear 714 may be coupled directly to rotating bar 518 such that rotation of smaller gear 714 results in a corresponding rotation of rotating bar 518.

Figure 8A:
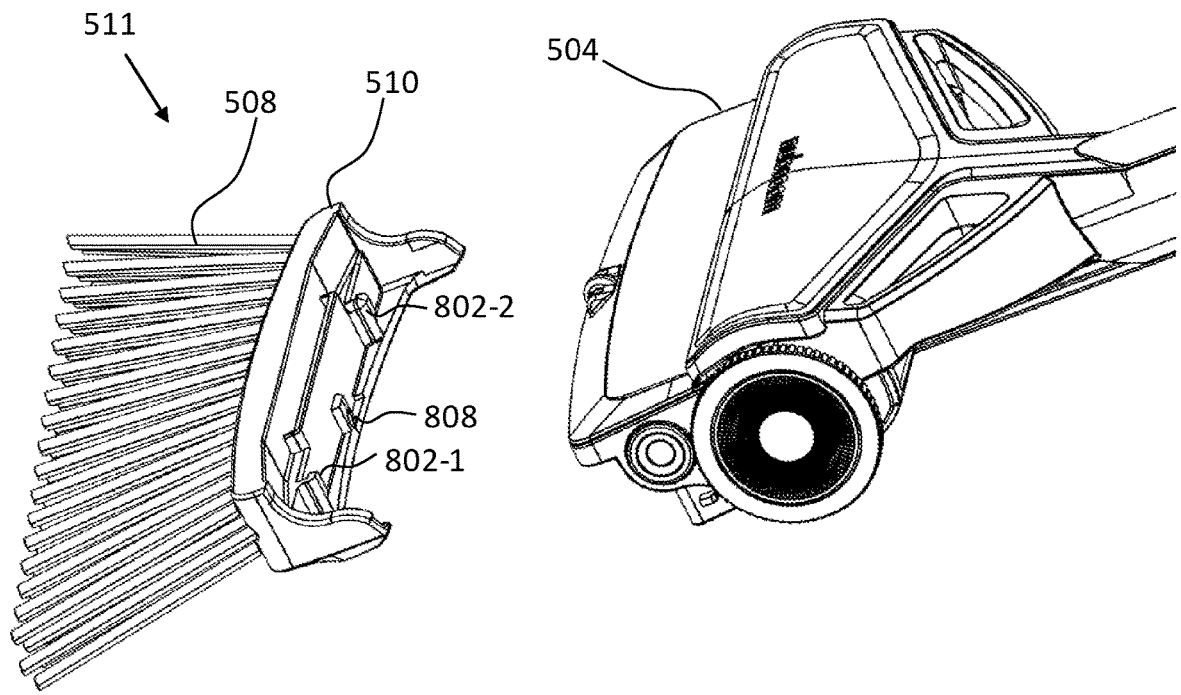
FIGS. 8A and 8B illustrate three-dimensional views of a broom head attachment, in accordance with some embodiments of the present disclosure.
Figure 8B:
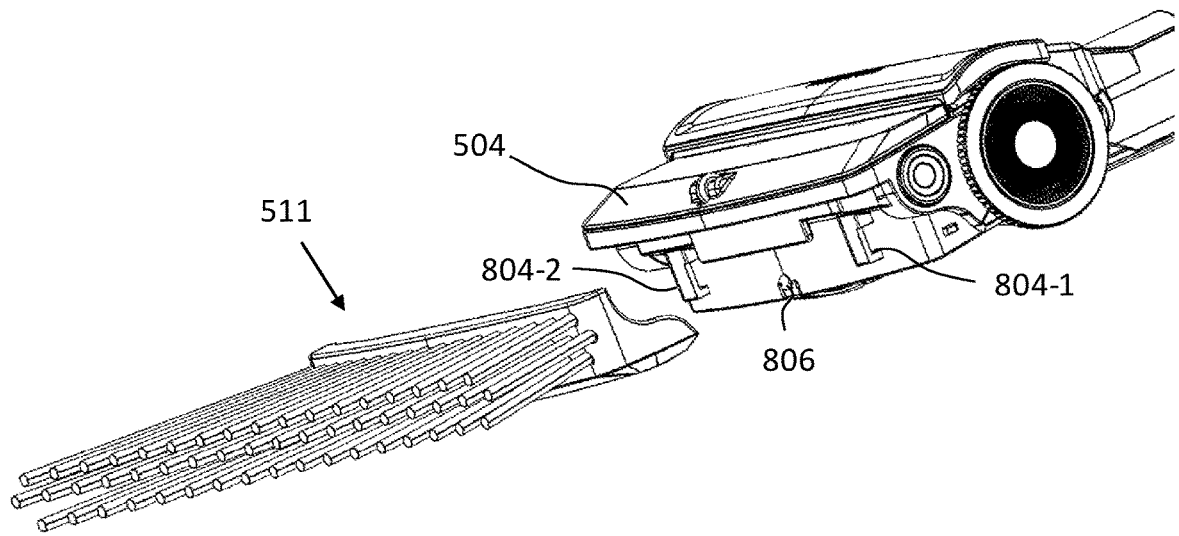

FIGS. 8A and 8B illustrate different views of removable broom module 511 having bristles 508 coupled to broom head 510, according to some embodiments. As noted previously, broom module 511 can be detached from housing 504 and replaced with another broom module having a different bristle pattern or design. According to some embodiments, bristles 508 are coupled to an outside surface of broom head 510 while an inside surface of broom head 510 includes one or more brackets that mechanically couple to corresponding brackets on housing 504. For example, broom head 510 may include two brackets 802-1 and 802-2 that slide sideways into corresponding brackets 804-1 and 804-2 of housing 504. A spring-loaded catch 806 on housing 504 may be used to engage with a corresponding indentation 808 in order to secure broom head 510 to housing 504. In some embodiments, spring-loaded catch 806 is mechanically coupled to lever assembly 503 on the underside of housing 504. Spring-loaded catch 806 may be disposed within curved housing 509 such that the coupling of lever assembly 503 into curved housing 509 also engages a distal end of lever assembly 503 with spring-loaded catch 806. In one example, movement of lever assembly 503 causes a corresponding retraction of spring-loaded catch 806 to allow broom head 510 to be detached from housing 504 (e.g., via laterally sliding broom head 510 off of housing 504). In another example, retraction of spring-loaded catch 806 is actuated via any other button or lever either on housing 504, elongated handle 501, or any part of lever assembly 503. In yet another example, spring-loaded catch 806 is not coupled to any other mechanism to retract it, such that the force of sliding broom module 511 sideways is enough to overcome the spring force and depress spring-loaded catch 806 to remove broom module 511 from housing 504.

Figure 8C:
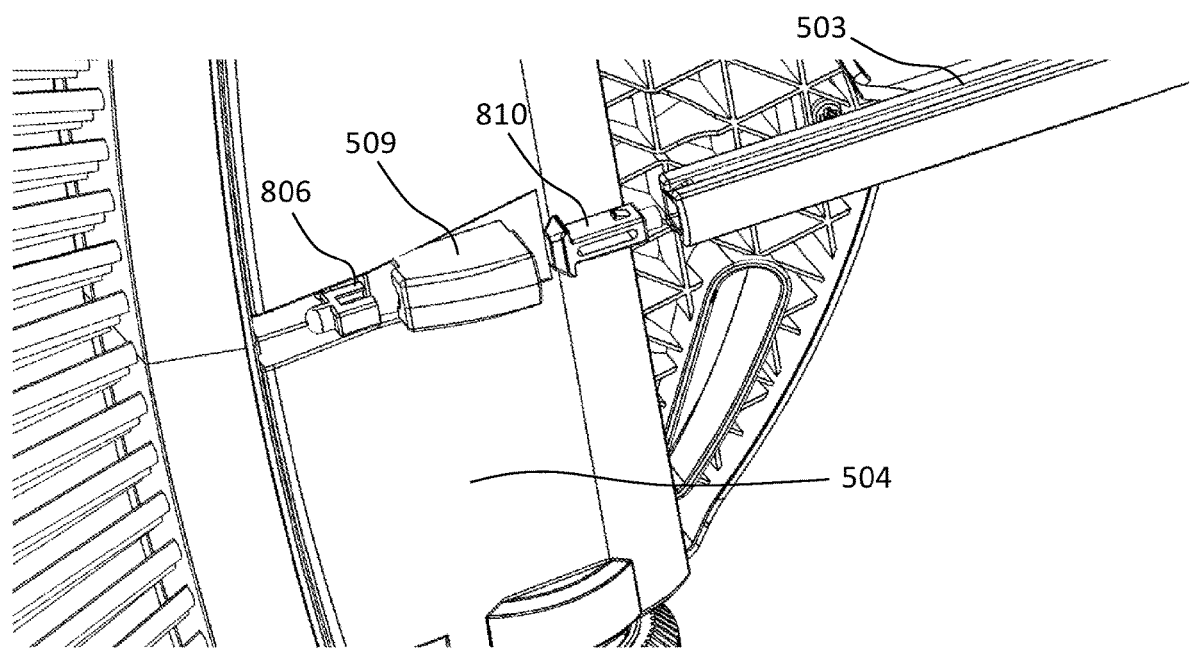
FIG. 8C illustrates an exploded view of an underside portion of the sweeping tool housing, in accordance with some embodiments of the present disclosure.

FIG. 8C illustrates an exploded view of a coupling mechanism for spring loaded catch 806 on an underside of housing 504, according to an embodiment. When cleaning assembly 502 is in the first state, lever assembly 503 couples to a push slider 810 within curved housing 509. In some embodiments, push slider 810 in turn is engaged with spring-loaded catch 806 within curved housing 509, and is designed to provide a push and/or pull motion on spring-loaded catch 806. In some other embodiments, push slider 810 is not coupled to spring-loaded catch 806 and they are both housed separately within curved housing 509.

Numerous specific details have been set forth herein to provide a thorough understanding of the embodiments. It will be understood in light of this disclosure, however, that the embodiments may be practiced without these specific details. In other instances, well known operations and components have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is a sweeping tool that includes an elongated handle having a proximal end and a distal end, a bracket coupled to the distal end of the elongated handle, and a cleaning assembly coupled to the bracket. The cleaning assembly is designed to rotate about an axis passing through a portion of the bracket to move between a first state and a second state. The cleaning assembly includes a housing, a broom head coupled to the housing, and a plurality of bristles coupled to the broom head. The housing is designed to hold a rotatable brush head and to collect debris swept up by the rotatable brush head when the cleaning assembly is in the second state. The plurality of bristles are oriented substantially parallel with the elongated handle when the cleaning assembly is in the first state.

Example 2 includes the subject matter of Example 1, wherein the broom head is removably coupled to the housing.

Example 3 includes the subject matter of Example 2, wherein the broom head is removably coupled to the housing via a spring-loaded catch and one or more brackets.

Example 4 includes the subject matter of anyone of Examples 1-3, wherein the cleaning assembly is configured to be locked into the first state where the plurality of bristles are oriented substantially parallel with the elongated handle.

Example 5 includes the subject matter of Example 4, wherein the cleaning assembly is configured to rotate about the axis and move into the second state where the plurality of bristles are oriented at an angle with respect to the elongated handle.

Example 6 includes the subject matter of Example 5, wherein the bracket is configured to rotate about the axis while the cleaning assembly is in the second state.

Example 7 includes the subject matter of Example 6, wherein the bracket is configured to rotate such that the elongated handle is substantially parallel with the plurality of bristles while the cleaning assembly is in the second state.

Example 8 includes the subject matter of anyone of Examples 1-7, wherein the elongated handle comprises a slidable component coupled to a lever assembly, wherein moving the slidable component causes a corresponding movement of the lever assembly that changes the cleaning assembly between the first state and the second state.

Example 9 includes the subject matter of Example 8, wherein the slidable component comprises a button that is depressed in order to move the slidable component axially along the elongated handle.

Example 10 includes the subject matter of Example 8 or 9, wherein the lever assembly engages with a catch on an underside of the housing when the cleaning assembly is in the first state.

Example 11 includes the subject matter of Example 10, wherein the lever assembly is disengaged from the catch when the cleaning assembly is in the second state.

Example 12 includes the subject matter of anyone of Examples 1-11, further comprising wheels coupled to the bracket, the wheels configured to contact a floor surface when the cleaning assembly is in the second state.

Example 13 includes the subject matter of Example 12, wherein the rotatable brush head is coupled to the wheels such that rotation of the wheels causes rotation of the rotatable brush head.

Example 14 includes the subject matter of Example 12 or 13, wherein at least one of the wheels includes a teethed portion that engages with a toothed gear coupled to the rotatable brush head.

Example 15 includes the subject matter of any one of Examples 12-14, wherein at least one of the wheels includes a torsion spring.

Example 16 includes the subject matter of any one of Examples 1-15, wherein the housing comprises a catch tray configured to collect debris captured by the rotatable brush head.

Example 17 includes the subject matter of Example 16, wherein the catch tray comprises a release door that is configured to swing open to release contents of the catch tray.

Example 18 is a broom module configured to be removably coupled to a housing. The broom module includes a broom head structure having an outer surface and an inner surface, a plurality of bristles coupled to an outer surface of the broom head structure, and one or more brackets coupled to an inner surface of the broom head. The one or more brackets are designed to removably engage with corresponding one or more brackets on a separate housing structure to secure the broom head structure to the separate housing structure.

Example 19 is a method of removing debris from a floor surface. The method includes sweeping debris into a pile using a sweeping tool that includes a broom head coupled to a housing, and a handle coupled to the housing; rotating the broom head to a position at least 30 degrees, 45 degrees, 60 degrees, 90 degrees or 120 degrees with respect to a length of the handle; and pushing a rotatable brush head over the pile, the rotatable brush head conveying the debris into a compartment, wherein the rotatable brush head is attached to the housing.

Example 20 includes the subject matter of Example 19 wherein the pushing causes rotation of the rotatable brush head.

What is claimed is:
1. A sweeping tool, comprising:
an elongated handle having a proximal end and a distal end;
a bracket coupled to the distal end of the elongated handle;
a cleaning assembly coupled to the bracket such that the cleaning assembly is configured to rotate about an axis passing through a portion of the bracket to move between a first state and a second state, the cleaning assembly comprising:

a housing configured to hold a rotatable brush head and to collect debris swept up by the rotatable brush head when the cleaning assembly is in the second state, a broom head coupled to the housing, and a plurality of bristles coupled to the broom head and oriented substantially parallel with the elongated handle when the cleaning assembly is in the first state; and wheels coupled to the rotatable brush head, the wheels configured to contact a floor surface when the cleaning assembly is in the second state.

2. The sweeping tool of claim 1, wherein the broom head is removably coupled to the housing.

3. The sweeping tool of claim 2, wherein the broom head is removably coupled to the housing via a spring-loaded catch and one or more brackets.

4. The sweeping tool of claim 1, wherein the cleaning assembly is configured to be locked into the first state where the plurality of bristles are oriented substantially parallel with the elongated handle.

5. The sweeping tool of claim 4, wherein the cleaning assembly is configured to rotate about the axis and move into the second state where the plurality of bristles are oriented at an angle with respect to the elongated handle.

6. The sweeping tool of claim 5, wherein the bracket is configured to rotate about the axis while the cleaning assembly is in the second state.

7. The sweeping tool of claim 6, wherein the bracket is configured to rotate such that the elongated handle is substantially parallel with the plurality of bristles while the cleaning assembly is in the second state.

8. The sweeping tool of claim 1, wherein the elongated handle comprises a slidable component coupled to a lever assembly, wherein moving the slidable component causes a corresponding movement of the lever assembly that changes the cleaning assembly between the first state and the second state.

9. The sweeping tool of claim 8, wherein the slidable component comprises a button that is depressed in order to move the slidable component axially along the elongated handle.

10. The sweeping tool of claim 8, wherein the lever assembly engages with a catch on an underside of the housing when the cleaning assembly is in the first state.

11. The sweeping tool of claim 10, wherein the lever assembly is disengaged from the catch when the cleaning assembly is in the second state.

12. The sweeping tool of claim 1, wherein rotation of the wheels causes a corresponding rotation of the rotatable brush head.

13. The sweeping tool of claim 1, wherein at least one of the wheels includes a teethed portion that engages with a toothed gear coupled to the rotatable brush head.

14. The sweeping tool of claim 1, wherein at least one of the wheels includes a torsion spring.

15. The sweeping tool of claim 1, wherein the housing comprises a catch tray configured to collect debris captured by the rotatable brush head.

16. The sweeping tool of claim 15, wherein the catch tray comprises a release door that is configured to swing open to release contents of the catch tray.

17. The sweeping tool of claim 16, further comprising a button on a side of the cleaning assembly, wherein pressing the button opens the release door.

18. The sweeping tool of claim 1, wherein the broom head has an outer surface and an inner surface, and the plurality of bristles are coupled to the outer surface of the broom head.

19. The sweeping tool of claim 18, wherein the broom head includes one or more brackets on the inner surface of the broom head, the one or more brackets being configured to engage with corresponding one or more brackets on the housing to secure the broom head to the housing.

20. The sweeping tool of claim 19, wherein the one or more brackets on the inner surface of the broom head are configured to slide laterally to engage with the one or more brackets on the housing.

* * * * *